(12) United States Patent
Elsen-Wahrer et al.

(10) Patent No.: US 10,328,009 B1
(45) Date of Patent: Jun. 25, 2019

(54) METHODS AND COMPOSITIONS FOR IMPROVING THE DURABILITY OF COLOR IN ARTIFICIALLY COLORED HAIR

(71) Applicant: L'OREAL, Paris (FR)

(72) Inventors: Andrea Elsen-Wahrer, Linden, NJ (US); Jim Singer, South Orange, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/940,116

(22) Filed: Mar. 29, 2018

(51) Int. Cl.
| | |
|---|---|
| *A61Q 5/10* | (2006.01) |
| *A61K 8/49* | (2006.01) |
| *A61K 8/20* | (2006.01) |
| *A61K 8/365* | (2006.01) |
| *A61K 8/22* | (2006.01) |

(52) U.S. Cl.
CPC .............. *A61K 8/4973* (2013.01); *A61K 8/20* (2013.01); *A61K 8/22* (2013.01); *A61K 8/365* (2013.01); *A61Q 5/10* (2013.01); *A61K 2800/43* (2013.01); *A61K 2800/884* (2013.01)

(58) Field of Classification Search
CPC ... A61Q 5/10; A61K 8/20; A61K 8/22; A61K 8/365; A61K 8/46; A61K 2800/43; A61K 2800/882
See application file for complete search history.

(56) References Cited

U.S. PATENT DOCUMENTS

2002/0189031 A1* 12/2002 Javet ..................... A61K 8/19
8/405

* cited by examiner

*Primary Examiner* — Eisa B Elhilo
(74) *Attorney, Agent, or Firm* — Polsinelli PC

(57) ABSTRACT

The present disclosure relates to compositions and methods for improving the quality and durability of color in artificially colored hair. The methods employ pre-color treatments containing divalent metal salts of inorganic acids; monovalent or divalent metal salts of organic acids; and antioxidants, wherein the pre-color treatments are applied to hair prior to artificially coloring hair.

30 Claims, No Drawings

METHODS AND COMPOSITIONS FOR IMPROVING THE DURABILITY OF COLOR IN ARTIFICIALLY COLORED HAIR

FIELD OF THE DISCLOSURE

The present disclosure relates to methods and compositions for providing color protection to hair, in particular, for improving artificial color deposit and the durability of color in artificially colored hair.

BACKGROUND

There are many products available for changing the natural color of hair. The process of changing the color of hair can involve either depositing an artificial color onto the hair, which provides a different shade or color to the hair, or lifting the color of the hair, such as for example, from a dark brown shade to a medium brown or a light brown shade. Hair color can be changed using permanent, semi-permanent, or temporary hair coloring products.

Many consumers desire a permanent color change and therefore use products containing permanent dyes. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Newly, permanently colored hair usually has a vibrant, shiny, and rich appearance. Unfortunately, however, in just a few short weeks, or in some cases even less, the color begins to fade due to washing, including shampooing, or exposure to environmental conditions. For instance, gorgeous rich brown colors become muddy and dull, beautiful shades of blonde turn brassy, and vibrant reds do not look so vibrant anymore acquiring golden, orange or brownish tonalities not desirable to the consumer. As described herein, the inventors of the instant disclosure have developed composition, methods and kits that improve color deposit onto hair and/or color durability by preventing color fading from hair. As described herein, the inventors of the instant disclosure have developed methods, compositions, and kits that improve color deposition and color durability by preventing color fading from hair.

SUMMARY OF THE DISCLOSURE

The present disclosure relates to methods of improving color deposit on hair and the durability of the color in artificially colored hair (e.g., improving the fade resistance and the longevity of the color). The methods described herein employ a combination of alkaline earth metal salts, alkali metal salts and antioxidants for use on hair before the hair is artificially colored or dyed. The inventors discovered a surprising improvement in color quality and durability when alkaline earth metal salts, alkali metal salts and antioxidants in the form of a pre-color treatment composition is applied onto hair shortly before application of a coloring composition to the hair. Antioxidants have long been used in coloring compositions, especially in hair coloring base compositions, which include oxidative dye precursors and optionally couplers. Historically, the purpose for including the antioxidants is to extend the shelf-life of coloring base compositions by preventing the oxidative dye precursors from becoming oxidized prematurely. The oxidative dye precursors must be preserved so they are available to penetrate the cuticle and cortex where the oxidation condensation reaction should occur. As hair coloring base compositions age, a percentage of the antioxidants deteriorate over time; the antioxidants deteriorate as they perform their anti-oxidizing action of donating electrons to neutralize free radicals.

The inventors discovered that treating or contacting hair with a combination of alkaline earth metal salts, alkali metal salts, and antioxidants before coloring hair improves the color quality and durability of the color in the hair. While not wishing to be bound by any particular theory, the inventors suspect that said combination function to prevent the oxidative dye precursors from reacting at the surface of the hair fibers. The antioxidants act to slow or prevent the oxidation condensation reaction from immediately occurring so that the oxidative dye precursors are able to more deeply penetrate the hair fibers. Once permanently lodged deep inside the hair fiber, the color is not easily removed. Therefore, the initial color quality and intensity that is achieved immediately upon artificially coloring the hair is maintained for longer periods of time.

In one aspect, the invention of the present disclosure is directed to a method for artificially coloring hair and inhibiting the coloring from fading, the method comprising:
(a) treating hair with a pre-color treatment composition comprising:
  at least 0.5 wt. % of one or more divalent metal salts of an inorganic acid;
  at least 0.5 wt. % of one or more monovalent or divalent metal salts of an organic acid; and
  at least 0.5 wt. % of one or more antioxidants;
  all weights being based on the total weight of the pre-color treatment composition; and
(b) treating the hair with a hair coloring composition comprising one or more colorants chosen from oxidative dye precursors, direct dyes, pigments, and mixtures thereof:
all weights being based on the total weight of the pre-color treatment composition.

The above-described hair coloring composition further comprises one or more oxidizing agents or is capable of being mixed with an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

The instant disclosure is also directed to pre-color treatment compositions comprising the one or more divalent metal salts of an inorganic acid, the one or more monovalent or divalent metal salts of an organic acid, and the one or more antioxidants.

In an embodiment, the one or more divalent metal salts of an inorganic acid and the one or more monovalent or divalent metal salts of an organic acid are contained in a first composition and the one or more antioxidants are contained in a second composition wherein the first and second composition are combined to form the pre-color treatment composition before use, the pre-color treatment composition being applied to hair before the hair is artificially colored.

In an embodiment, the one or more divalent metal salts of an inorganic acid, the one or more monovalent or divalent metal salts of an organic acid, and the one or more antioxidants are contained in three separate compositions wherein all three compositions are combined to form the pre-color treatment composition before use, the pre-color treatment composition being applied to hair before the hair is artificially colored.

The instant disclosure also relates to kits comprising the various compositions used to carry out the methods described herein. The kits may be used by hair-care professionals and salons for treating the hair of patrons or the kits may be purchased and used at home directly by consumers.

It is to be understood that both the foregoing general description and the following detailed description are exemplary and explanatory only, and are not restrictive of the disclosure.

Other subjects, characteristics, aspects and advantages of embodiments of the disclosure will emerge even more clearly on reading the description and the various examples that follow.

DETAILED DESCRIPTION OF THE DISCLOSURE

As used herein, the expression "one or more" means at least one and thus includes individual components as well as mixtures/combinations.

The terms "a," "an," and "the" are understood to encompass the plural as well as the singular.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" or "containing" and not in the exclusive sense of "consisting only of".

As used herein, the terms "applying a composition onto hair" and all its grammatical variations, include "contacting hair with a composition" or "exposing hair to a composition" or "layering a composition onto hair" or "treating hair with a composition" with any suitable means, for example, by using the hands or fingers, or an applicator such as a brush or comb, or by spraying, or by delivering through a nozzle or bottle cap tip.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The terms "organic acid" mean compounds containing carbon atoms and hydrogen atoms and optionally heteroatoms such as S, O, N or P, alone or in combination.

When referring to "compositions described herein," all types of compositions are intended unless specifically described otherwise. The "compositions disclosed herein" include the compositions comprising one or more reducing agent, the composition comprising one or more lactones, to oxidizing compositions, etc.

The compositions and methods of the present disclosure can comprise, consist of, or consist essentially of the essential elements and limitations of the disclosure described herein, as well as any additional or optional ingredients, components, or limitations described herein or otherwise useful.

An embodiment of the present disclosure is directed to a method for artificially coloring hair and inhibiting the coloring from fading, the method comprising:
(a) treating hair with a pre-color treatment composition comprising:
at least 0.5 wt. % of one or more divalent metal salts of an inorganic acid;
at least 0.5 wt. % of one or more monovalent or divalent metal salts of an organic acid; and
at least 0.5 wt. % of one or more antioxidants;
all weights being based on the total weight of the pre-color treatment composition; and
(b) treating the hair with a hair coloring composition comprising one or more colorants chosen from oxidative dye precursors, direct dyes, pigments, and mixtures thereof:
all weights being based on the total weight of the pre-color treatment composition.

An embodiment of the present disclosure is directed to a method for artificially coloring hair and inhibiting the coloring from fading, the method comprising:
(a) treating hair, before artificially coloring hair, with:
i. about 0.5 wt. % to about 50 wt. % of one or more divalent metal salts of an inorganic acid; and
ii. about 0.5 wt. % to about 50 wt. % of one or more monovalent or divalent metal salts of an organic acid;
iii. about 0.5 wt. % to about 50 wt. % of one or more antioxidants; and
(b) treating the hair with a hair coloring composition comprising one or more colorants chosen from oxidative dye precursors, direct dyes, pigments, and mixtures thereof;
all weights being based on the total weight of the pre-color treatment composition;
wherein the one or more divalent metal salts of an inorganic acid (i), the one or more monovalent or divalent metal salts of an organic acid (ii), and the one or more antioxidants (iii) are applied together or separately onto the hair.

In an embodiment, the one or more divalent metal salts of an inorganic acid (i), the one or more monovalent or divalent metal salts of an organic acid (ii), and the one or more antioxidants (iii) together or separately, are contained in cosmetically acceptable solvent(s).

In an embodiment, the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

In an embodiment, the one or more antioxidants are chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof.

In an embodiment, the pre-color treatment composition comprises one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; one or more divalent metal salts of an organic acid chosen from zinc lactate, zinc gluconate, zinc phenolsulfonate, zinc salicylate, zinc pyrrolidone carboxylic acid (Zinc PCA), zinc ascorbate, their derivatives thereof, and mixtures thereof; and one or more antioxidants chosen from ascorbic acid and its derivatives, sodium sulfite, sodium metabisulfite, sodium hydrosulfite, tocopheryl acetate, tocopherols, alpha-tocopherol, isoascorbic acid, magnesium ascorbyl phosphate, ascorbyl glucoside, and mixtures thereof.

In an embodiment, the pre-color treatment composition comprises one or more divalent metal salts of an inorganic acid chosen from calcium chloride, one or more divalent metal salts of an organic acid chosen from zinc gluconate, and one or more antioxidants chosen from ascorbic acid.

In an embodiment of the present disclosure, the pre-color treatment composition for use in the above-described methods contains:

(a) one or more divalent metal salts of an inorganic acid present in an amount of from about 0.5 wt. % to about 50 wt. % based on the total weight of the pre-color treatment composition;

(b) one or more divalent metal salts of an organic acid present in an amount of from about 0.5 wt. % to about 50 wt. %, based on the total weight of the pre-color treatment composition; and (c) one or more antioxidants present in an amount of from about 0.5 wt. % to about 50 wt. %, based on the total weight of the pre-color treatment composition.

In an embodiment, of the present disclosure, the pre-color treatment composition for use in the above-described methods contains:

(a) one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof;

(b) one or more monovalent or divalent metal salts of an organic acid chosen from zinc lactate, zinc gluconate, zinc phenolsulfonate, zinc salicylate, zinc pyrrolidone carboxylic acid (Zinc PCA), zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof; and (c) one or more antioxidants chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof.

In an embodiment, the pre-color treatment composition further comprises one or more of a thickening agent, a cationic agent, a surfactant, a silicone, and a cosmetically acceptable solvent.

In an embodiment, the pre-color treatment composition comprises a first composition containing the one or more divalent metal salts of an inorganic acid and the one or more monovalent or divalent metal salts of an organic acid; and a second composition containing the one or more antioxidants; wherein the first and the second compositions are combined within 2 hours before artificially coloring hair. In an embodiment, the first composition further comprises one or more of a thickening agent, a cationic agent, a surfactant, a silicone, and a cosmetically acceptable solvent. In an embodiment, the second composition further comprises one or more of a thickening agent, a cationic agent, a surfactant, a silicone, and a cosmetically acceptable solvent In an embodiment, the weight ratio of the one or more divalent metal salts of an inorganic acid to the one or more monovalent or divalent metal salts of an organic acid is from about 10:1 to about 1:10 or from about 8:1 to about 1:8 or from about 5:1 to about 1:5 or from about 3:1 to about 1:3 or from about 2:1 to about 1:2, including ranges and sub-ranges therebetween, or at about 1.

In an embodiment, the amount of the one or more divalent metal salts of an inorganic acid is greater than the amount of the one or more monovalent or divalent metal salts of an organic acid; for example, the weight ratio of the one or more divalent metal salts of an inorganic acid to the one or more monovalent or divalent metal salts of an organic acid can be 10:1, or 9:1, or 8:1, or 7:1, or 6:1, or 5:1, or 4;1, or 3;1, or 2:1.

In an embodiment, the amount of the one or more divalent metal salts of an inorganic acid is less than the amount of the one or more monovalent or divalent metal salts of an organic acid; for example, the weight ratio of the one or more divalent metal salts of an inorganic acid to the one or more monovalent or divalent metal salts of an organic acid can be 1:10, or 1:9, or 1:8, or 1:7, or 1:6, or 1:5, or 1:4, or 1:3, or 1:2.

In an embodiment, upon treating the hair with the pre-color treatment composition in (a), the pre-color treatment composition is allowed to remain on the hair for about 1 minute to about 1 hour or up to about 10 minutes, or up to about 20 minutes, or up to about 30 minutes, or up to about 45 minutes, at a temperature of about 20° C. to about 45° C. before treating the hair with the hair coloring composition in (b).

In an embodiment, the hair treated with the pre-color treatment composition is not rinsed or washed with water before the hair is colored.

In an embodiment of the present disclosure, the invention is directed to a kit for artificially coloring hair, the kit comprising:

(i) a pre-color treatment component comprising one or more divalent metal salts of an inorganic acid; one or more monovalent or divalent metal salts of an organic acid; and one or more antioxidants;

(ii) a hair coloring composition comprising one or more colorants chosen from oxidative dye precursors, direct dyes, pigments, and mixtures thereof;

(iii) an oxidizing composition comprising: (i) one or more oxidizing agents; and (iv) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof; and
wherein the one or more divalent metal salts of an inorganic acid, the one or more monovalent or divalent metal salts of an organic acid, and the one or more antioxidants are packaged as separate compositions or together as a single composition.

In various embodiments and/or in accordance with various use instructions, the contents of the pre-color treatment component in the above-described kit are to be applied onto hair such that the total amount of the metal salts applied onto the hair ranges from about 1 wt. % to about 60 wt. %, or such as from about 1 wt. % to about 50 wt. %, or such as from about 1 wt. % to about 40 wt. %, or such as from about 1 wt. % to about 30 wt. %, or such as from about 1 wt. % to about 20 wt. %, or such as from about 1 wt. % to about 15 wt. %, or such as from about 5 wt. % to about 15 wt. %, or such as from about 5 wt. % to about 10 wt. %, including all ranges and sub-ranges, and the total amount of antioxidants ranges from about 1 wt. % to about 50 wt. %, or such as from about 1 wt. % to about 40 wt. %, or such as from about 1 wt. % to about 30 wt. %, or such as from about 5 wt. % to about 25 wt. %, or such as from about 10 wt. % to about 20 wt. %, including all ranges and sub-ranges, all weights based on the total weight of the pre-color treatment composition.

In some embodiments, the amount of the antioxidant in the final hair coloring composition-oxidizing composition (developer) mixture or ready-to-use dye mixture is such that the temperature of the mixture is not higher than body temperature or about 37° C. This final amount can also depend on the mixing container or device employed. For example, lower amounts of antioxidant can be employed when hair coloring composition and developer are mixed in a bottle and higher amounts can be employed when mixing is performed in a bowl and an applicator is generally used to dye the hair.

The above-described hair coloring compositions further comprise one or more oxidizing agents or is capable of being mixed with an oxidizing composition (also called developer composition) comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

The above-described hair coloring compositions further comprise alkalizing agents. Non-limiting examples of alkalizing agents that may be included in the hair coloring compositions include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof.

In an embodiment, pre-color treatment composition of the present invention further comprises:
  one or more of a thickening agent chosen from cellulose and cellulose derivatives, guar and guar derivatives, starch and starch derivatives, acrylic or acrlyates based polymers, gums, and mixtures thereof;
  a cationic agent chosen from cationic surfactants;
  a surfactant chosen from alkoxylated fatty alcohols, fatty alcohols, and mixtures thereof, preferably chosen from fatty alcohols;
  a silicone chosen from amino silicones, non-amino silicones, and mixtures thereof; preferably chosen from amino silicones; and
  a cosmetically acceptable solvent.

It has now been surprisingly and unexpectedly discovered that the use of the compositions, methods, and kits of the present disclosure resulted in good deposit of artificial color onto hair as well as durable artificial color wherein the fading of the artificial was found to be minimal even over several shampooings of the hair.

Divalent Metal Salts of an Inorganic Acid

The one or more divalent metal salts of an inorganic acid may be chosen from metal halides, metal hydroxides, metal sulfates, metal oxides, and mixtures thereof.

The divalent metals with which the metal salts are formed are calcium, zinc, iron, nickel, copper, silver, magnesium, strontium, barium, manganese, cobalt, and mixtures thereof.

Suitable examples of the one or more divalent metal salts of an inorganic acid may be chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more divalent metal salts of an inorganic acid includes a calcium salt.

In an embodiment, the calcium salt is calcium chloride.

The one or more divalent metal salts of an inorganic acid of the present disclosure may be employed in an amount of from about 0.5 wt. % to about 50 wt. % or from about 0.5 wt. % to about 45 wt. % or from about 0.5 wt. % to about 45 wt. % or from about 0.5 wt. % to about 40 wt. % or from about 1 wt. % to about 40 wt. %, or from about 1.5 wt. % to about 35 wt. %, or from about 2 wt. % to about 30 wt. %, or from about 2.5 wt. % to about 30 wt. %, or from about 3 wt. % to about 25 wt. %, or from about 3 wt. % to about 20 wt. %, or from about 3 wt. % to about 15 wt. %, or from about 3 wt. % to about 10 wt. %, including all ranges and sub-ranges therebetween, based on the total weight of the pre-color treatment composition.

In various embodiments, the one or more divalent metal salts of the present disclosure is employed in a wt. % amount of about 0.5, 0.75, 1, 1.25, 1.5, 1.75, 2, 2.25, 2.5, 2.75, 3, 3.25, 3.5, 3.75, 4, 4.2, 4.5, 4.75, 5, 5.25, 5.5, 5.75, 6.25, 6.5, 6.75, 7, 7.25, 7.5, 7.75, 8, 8.25, 8.5, 8.75, 9, 9.25, 9.5, 9.75, 10, 11, 12, 14, 15, 16, 18, 20, 22, 24, 25, 26, 28, 30, 32, 34, 35, 36, 38, 40, 42, 44, 45, 46, 48, or 50 wt. %, based on the total weight of the pre-color treatment composition.

Monovalent or Divalent Metal Salts of an Organic Acid

The one or more monovalent or divalent metal salts of an organic acid may be chosen from metal salts wherein the organic acid is chosen from C1 to C9 monocarboxylic or di-carboxylic acids, polycarboxylic acids, hydroxy-carboxylic acids, and fatty acids having at least 10 carbon atoms including organic acids with heterocyclic groups, for example, ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid.

Suitable examples monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc ascorbate, zinc citrate, their salt derivatives thereof, and mixtures thereof.

In an embodiment, the one or more divalent metal salts of an organic acid includes a zinc salt.

In an embodiment, the zinc salt is zinc gluconate.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

The one or more monovalent or divalent metal salts of an organic acid of the present disclosure may be employed in an amount of from 0.5 wt. % to about 50 wt. % or from about 0.5 wt. % to about 45 wt. % or from about 0.5 wt. % to about 45 wt. % or from about 0.5 wt. % to about 40 wt. % or from about 1 wt. % to about 40 wt. %, or from about 1.5 wt. % to about 35 wt. %, or from about 2 wt. % to about 30 wt. %, or from about 2.5 wt. % to about 30 wt. %, or from about 3 wt. % to about 25 wt. %, or from about 3 wt. % to about 20 wt. %, or from about 3 wt. % to about 15 wt. %, or from about 3 wt. % to about 10 wt. %, including all ranges and sub-ranges therebetween, based on the total weight of the pre-color treatment composition.

In various embodiments, the one or more monovalent or divalent metal salts of an organic acid of the present disclosure is employed in a wt. % amount of about 0.5, 0.75, 1, 1.25, 1.5, 1.75, 2, 2.25, 2.5, 2.75, 3, 3.25, 3.5, 3.75, 4, 4.2, 4.5, 4.75, 5, 5.25, 5.5, 5.75, 6.25, 6.5, 6.75, 7, 7.25, 7.5, 7.75, 8, 8.25, 8.5, 8.75, 9, 9.25, 9.5, 9.75, 10, 11, 12, 14, 15, 16, 18, 20, 22, 24, 25, 26, 28, 30, 32, 34, 35, 36, 38, 40, 42, 44, 45, 46, 48, or 50 wt. %, based on the total weight of the pre-color treatment composition.

Antioxidants

Many antioxidants that are useful in hair coloring base compositions. For example, non-limiting examples of antioxidants include ascorbic acid, sodium sulfite, sodium metabisulfite, sodium hydrosulfite, tocopherols, alpha-tocopherol, tocopheryl acetate, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, and a mixture thereof. The selection of appropriate antioxidant(s) useful in a particular antioxidant booster composition may depend on a variety of factors, for example, the type of oxidative dye precursors of the hair coloring base composition, the types of optional couplers that may be present in the hair coloring base composition, etc. In some instances, the antioxidant booster composition includes ascorbic acid, sodium sulfite, sodium metabisulfite, or a mixture thereof.

The antioxidants may include flavonoids. Flavonoids exhibit chelating properties with metal ions and may reduce the oxidative damage from metal ions by sequestering the ions. Formation and stability of flavonoids-metal-chelates is a structure-dependent function. Flavonoids with a catechol moiety and with hydrogen bonds between hydroxyl group in the 5- and 3-positions have chelating properties.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, emblica *officinalis*, and bioflavonoids from rose hip and citrus may be used including watersoluble bioflavonoids such as hesperidin methyl chalcone may also be used.

Other antioxidants, which may be incorporated, include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ.-tocotrienol, d-delta-tocotrienol,) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E and other carotenoids.

The flavonoid may be a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals. The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C., and synthetic Safalcone.

The one or more antioxidants of the present disclosure may be employed in an amount of from 0.5 wt. % to about 50 wt. % or from about 0.5 wt. % to about 45 wt. % or from about 0.5 wt. % to about 45 wt. % or from about 0.5 wt. % to about 40 wt. % or from about 1 wt. % to about 40 wt. %, or from about 1.5 wt. % to about 35 wt. %, or from about 2 wt. % to about 30 wt. %, or from about 2.5 wt. % to about 30 wt. %, or from about 3 wt. % to about 25 wt. %, or from about 4 wt. % to about 20 wt. %, or from about 5 wt. % to about 15 wt. %, or from about 5 wt. % to about 10 wt. %, including all ranges and sub-ranges therebetween, based on the total weight of the pre-color treatment composition.

In various embodiments, the one or more antioxidants of the present disclosure is employed in a wt. % amount of about 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6.25, 6.5, 6.75, 7, 7.25, 7.5, 7.75, 8, 8.25, 8.5, 8.75, 9, 9.25, 9.5, 9.75, 10, 10.5, 11, 11.5, 12, 12.5, 13, 13.5, 14, 14.5, 15, 15.5, 16, 16.5, 16.7, 18, 18.5, 19, 19.5, 20, 20.5, 21, 21.5, 22, 22.5, 23, 23.5, 24, 24.5, 25, 25.5, 26, 27, 28, 29, 30, 32, 34, 35, 36, 38, 40, 42, 44, 45, 46, 48, or 50 wt. %, based on the total weight of the pre-color treatment composition.

Colorants

The coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N, N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyoxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-l, N,N'-bis(.beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(.beta.-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyloxy)benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta.-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

(Va)

(V'a)

(VIa)

(VI'a)

and

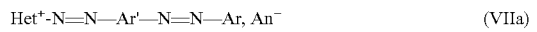(VIIa)

in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het$^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

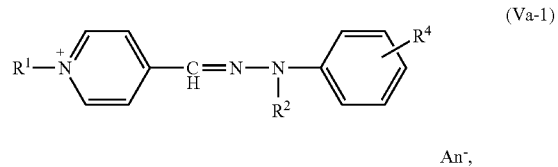

(Va-1)

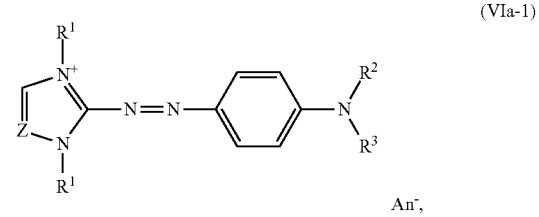

(VIa-1)

Formulae (V-1) and (VI-1) with

R$^1$ representing a (C$_1$-C$_4$) alkyl group such as methyl;
R$^2$ and R$^3$, which are identical or different, represent a hydrogen atom or a (C$_1$-C$_4$)alkyl group, such as methyl; and
R$^4$ represents a hydrogen atom or an electron-donating group such as optionally substituted (C$_1$-C$_8$)alkyl, optionally substituted (C$_1$-C$_8$)alkoxy, or (di)(C$_1$-C$_8$)(alkyl)amino optionally substituted on the alkyl group(s) with a hydroxyl group; particularly, R$^4$ is a hydrogen atom,
Z represents a CH group or a nitrogen atom, preferentially CH;
An$^-$ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

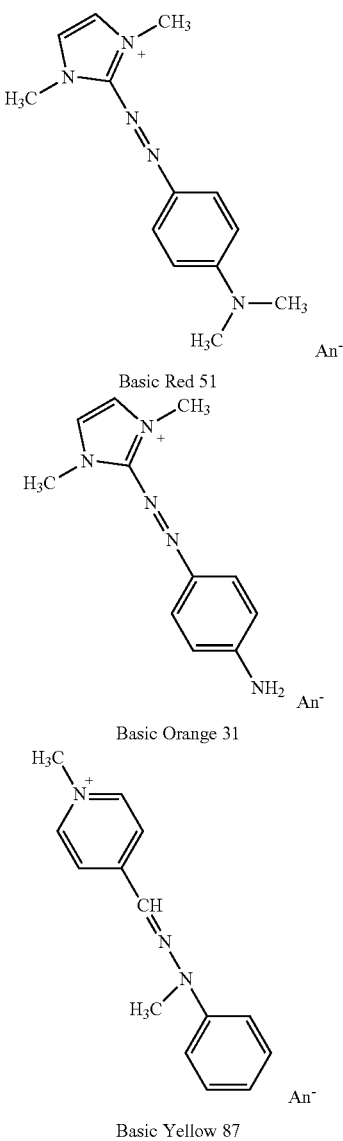

Basic Red 51

Basic Orange 31

Basic Yellow 87

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Alkalizing Agents

The hair coloring composition may have a pH that is alkaline. Exemplary pH's include 7, 8, 9, 10, 11, 12, 13 or 14. In some embodiments, the pH of the hair coloring composition may range from about 7, 8, or 9 to about 9, 10, 11 or 12.

The alkalinity of the hair coloring composition may be derived from one or more alkalizing agents. In some embodiments, the alkalizing agent may ammonia or an ammonia gas-generating compound and/or an amine or ammonium-based compound in amounts sufficient to make such compositions alkaline. In further embodiments, the alkalizing agent may be selected from alkanolamines, such as monoethanolamine (MEA) and isopropanolamine. Alkalinity may be derived from ammonium compounds as well (e.g., NH$_4$OH).

The one or more alkalizing agents may be present in amounts ranging from greater than about 0, or from 1, 2, 3, 4, 5, 10 to about 5, 10, 13, 15, 18, 20, 25 or 30% by weight of the total composition.

Oxidizing Agents

Oxidizing agents may be selected from, for example, peroxides, persulfates, perborates percarbonates, alkali metal bromates, ferricyanides, peroxygenated salts, or mixtures thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is hydrogen peroxide present in an aqueous solution whose titre may range from 1 to 40 volumes, such as from 5 to 40 volumes or such as from 5 to 20 volumes.

In other cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. Hydrogen peroxide may commonly be used as the oxidizing agent.

In an embodiment, the oxidizing agent is hydrogen peroxide and is provided as an oxidizing (developer) composition.

In general, the oxidizing agent will be present in an amount of from about 0.05 to about 50% by weight, such as from about 0.1% to about 30% by weight, or such as from about 0.1% to about 20% by weight, or such as from about 1% to about 10% by weight, based on the total weight of the oxidizing composition.

In some instances, the oxidizing composition is aqueous or is in the form of an emulsion.

In other instances, the oxidizing composition is substantially anhydrous. The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof. When the oxidizing composition is substantially anhydrous, the oxidizing composition may comprise at least one solvent chosen from organic solvents. Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvent may, for example, be present in an amount ranging from about 0.5% to about 70% by weight, such as from about 2% to about 60% by weight, preferably from about 5 to about 50% by weight, relative to the total weight of the oxidizing composition.

The oxidizing composition may be in the form of a powder, gel, liquid, foam, lotion, cream, mousse, and emulsion.

The oxidizing composition of the present disclosure my also contain at least one fatty substance as described above. Thus, the total amount of fatty substances in the combination or mixture of the coloring and oxidizing compositions of the present disclosure may range from about 10% to about 80% by weight, or such as from about 20% to about 60% by weight, or such as from about 20% to about 40% by weight, or such as from about 20% to about 30% by weight, based on the total weight of the composition.

Cosmetically Acceptable Solvent (or Carrier)

The compositions of the present disclosure such as the pre-color treatment composition and the hair coloring composition may be presented in a cosmetically acceptable solvent. This cosmetically acceptable solvent may include, for example, water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The organic solvents for use in the present disclosure can be volatile or non-volatile compounds.

The cosmetically acceptable solvent may be employed according to the present disclosure in an amount ranging from about 5% to about 95% by weight, or such as from about 20% to about 90% by weight, such as from about 30 to about 80% by weight, or such as from about 35% to about 75% by weight, such as from about 5 to about 50% by weight, such as from about 50 to 95% by weight, based on the total weight of the composition.

The organic solvent may be employed according to the present disclosure in an amount ranging from about 0.1% to about 25% by weight, such as from about 1% to about 15% by weight, or such as from about 3% to about 10% by weight, or such as from about 5% to about 10% by weight, based on the total weight of the composition of the present disclosure.

Auxiliary Agents

Auxiliary ingredients may be added to the pre-color treatment, hair coloring and/or oxidizing (developer) compositions of the present disclosure. Exemplary auxiliary ingredients useful according to various embodiments of the disclosure include, but are not limited to, thickening agents (including rheology-modifying and viscosity modifying agents agents), cationic agents (including cationic surfactants and cationic polymers), anionic, non-ionic and/or amphoteric/zwitterionic surfactants, bleach activators and co-bleach activators, chelants, fatty substances, ceramides, silicones, and lift-enhancing agents, such as nitrogen-containing compounds and metal catalyst compounds, and preservatives.

The compositions may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

Thickening Agents

The compositions of the present disclosure may contain one or more thickening agents which include rheology or viscosity modifying agents, such as viscosity increasing agents. Classes of such agents include, but are not limited to, viscous liquids, such as polyethylene glycol, thickening polymers, such as cellulose derivatives (for example, hydroxyethyl cellulose, hydroxypropyl methylcellulose), guar and guar derivatives such hydroxypropyl guar, and acrylic acid and/or acrylate based polymers (for example, carbomers, Carbopol and Pemulen types), poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, starches and starch derivatives such as hydroxypropyl starch phosphate, particulate associate colloids and clays/silicate clays, such as bentonite, laponite, colloidal silicon dioxide, and microcrystalline cellulose, and salts, such as sodium chloride, and mixtures thereof.

The thickening agents may, for example, be present in an amount ranging from about 0.1% to about 20% by weight, such as from about 0.2% to about 15% by weight, or from about 0.3% to about 10% by weight, or from about 0.4% to about 8% by weight, or from about 0.5% to about 6% by weight, based on the total weight of the compositions of the present disclosure.

Cationic Agents

The various compositions described herein may include one or more cationic agents such as cationic surfactants and cationic polymers.

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl tri hydroxyethyl propylenediamine dihydrofluoride, tallowtrimonium chloride, and hexadecyltrimethyl ammonium bromide.

The cationic surfactant(s) may be chosen from optionally polyoxyalkylenated, primary, secondary or tertiary fatty amines, or salts thereof, and quaternary ammonium salts, and mixtures thereof.

The fatty amines generally comprise at least one C8-C30 hydrocarbon-based chain.

Examples of quaternary ammonium salts that may especially be mentioned include: those corresponding to the general formula (A) below:

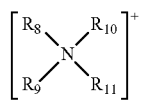

(A)

in which the groups R8 to R11, which may be identical or different, represent a linear or branched, saturated or unsaturated aliphatic group comprising from 1 to 30 carbon atoms, or an aromatic group such as aryl or alkylaryl, at least one of the groups R8 to R11 denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from C1-C30 alkyl, C2-C30 alkenyl, C1-C30 alkoxy, polyoxy(C2-C6) alkylene, C1-C30 alkylamide, (C12-C22)alkylamido(C2-C6)alkyl, (C12-C22)alkyl acetate and C1-C30 hydroxyalkyl groups; X– is an anion chosen from the group of halides, phosphates, acetates, lactates, (C1-C4)alkyl sulfates, and (C1-C4)alkyl- or (C1-C4)alkylarylsulfonates.

Among the quaternary ammonium salts of formula (A), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

In some cases it is useful to use salts such as the chloride salts of the following compounds:

A. a quaternary ammonium salt of imidazoline, such as, for example, those of formula (B) below:

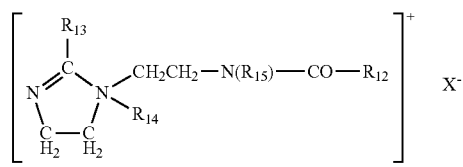

(B)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo;

B. a quaternary diammonium or triammonium salt, in particular of formula (C):

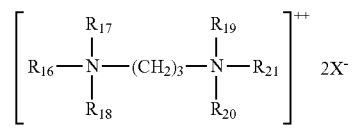

(C)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, FINQUAT CT-P, sold by the company FINETEX (Quaternium 89), and FINQUAT CT, sold by the company FFINETEX (Quaternium 75), C. a quaternary ammonium salt containing at least one ester function, such as those of formula (D) below:

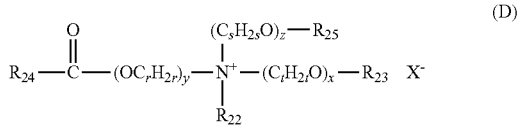

in which:

R$_{22}$ is chosen from C$_1$-C$_6$ alkyl groups and C$_1$-C$_6$ hydroxyalkyl or dihydroxyalkyl groups;

R$_{23}$ is chosen from:

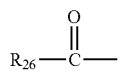

R$_{27}$, which is a linear or branched, saturated or unsaturated C$_1$-C$_{22}$ hydrocarbon-based group, and a hydrogen atom, R$_{25}$ is chosen from:

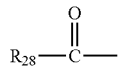

R$_{23}$, which is a linear or branched, saturated or unsaturated C$_1$-C$_6$ hydrocarbon-based group, and a hydrogen atom, R24, R26 and R28, which may be identical or different, are chosen from linear or branched, saturated or unsaturated C7-C21 hydrocarbon-based groups;

r, s and t, which may be identical or different, are integers ranging from 2 to 6;

y is an integer ranging from 1 to 10;

x and z, which may be identical or different, are integers ranging from 0 to 10;

X– is a simple or complex, organic or mineral anion;

with the proviso that the sum x+y+z is from 1 to 15, that when x is 0 then Rn denotes R27, and that when z is 0 then R25 denotes R29.

The alkyl groups R22 may be linear or branched, and more particularly linear. In some cases, R22 denotes a methyl, ethyl, hydroxyethyl or dihydroxypropyl group, and more particularly a methyl or ethyl group. Advantageously, the sum x+y+z is from 1 to 10.

When R23 is a hydrocarbon-based group R27, it may be long and contain from 12 to 22 carbon atoms, or may be short and contain from 1 to 3 carbon atoms. When R25 is an R29 hydrocarbon-based group, it preferably contains 1 to 3 carbon atoms. Advantageously, R24, R26 and R28, which may be identical or different, are chosen from linear or branched, saturated or unsaturated C11-C21 hydrocarbon-based groups, and more particularly from linear or branched, saturated or unsaturated C11-C21 alkyl and alkenyl groups.

In some cases, x and z, which may be identical or different, have values of 0 or 1. Likewise, in some cases y is equal to 1. In some cases, r, s and t, which may be identical or different, are equal to 2 or 3, and even more particularly are equal to 2.

The anion X– is may be a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion X– is even more particularly chloride or methyl sulfate.

Use is made more particularly, in the composition according to the invention, of the ammonium salts of formula (D) in which:

R$_{22}$ denotes a methyl or ethyl group, x and y are equal to 1;

z is equal to 0 or 1;

r, s and t are equal to 2;

R$_{23}$ is chosen from:

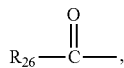

methyl, ethyl or C$_{14}$-C$_{22}$ hydrocarbon-based groups, and a hydrogen atom;

R$_{25}$ is chosen from:

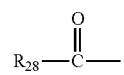

and a hydrogen atom;

R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups. The hydrocarbon-based groups are advantageously linear.

Mention may be made, for example, of the compounds of formula (D) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with C10-C30 fatty acids or with mixtures of C10-C30 fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin. Such compounds are, for example, sold under the names DEHYQUART by the company Henkel, STEPANQUAT by the company Stepan, NOXAMIUM by the company Ceca or REWOQUAT WE 18 by the company Rewo-Witco.

The composition according to the invention may contain, for example, a mixture of quaternary ammonium monoester, diester and triester salts with a weight majority of diester salts.

Use may be made of behenoylhydroxypropyltrimethylammonium chloride.

Non-limiting examples of other cationic surfactants that can be used in the current compositions include dimethylamine derivatives, such as for example stearyl dimethyl amine, stearamidoproppyl dimethylamine, brassicamidopropyl dimethylamine, and mixtures thereof.

In an embodiment the cationic surfactant is selected from stearamidopropyl dimethylamine, commercially available under the tradename MACKINE 301, from Rhodia.

Cationic Polymers

The cationic polymers may be derived from polysaccharides, for example cationic cellulose derivatives, cationic starch derivatives, cationic guar derivatives and cationic locust bean gum derivatives, synthetic cationic polymers, mixtures or combinations of these agents. The compositions may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

Non-limiting examples of cationic polymers suitable for us in the compositions of the disclosure are polyquaternium compounds such as the diallyidimethylammonium chloride/ acrylic acid copolymers sold under the names MERQUAT 280 POLYMER or MERQUAT 280NP POLYMER or MERQUAT 281 POLYMER or MERQUAT 295 POLYMER, by the company Nalco (Lubrizol) (INCI name: Polyquaternium-22); the copolymer of methacrylamidopropyltrimonium chloride, of acrylic acid and or methyl acrylate, sold under the name MERQUAT 2001 POLYMER OR MERQUAT 2001N POLYMER by the company Nalco (Lubrizol) (INCI name: Polyquaternium-47); the acrylamide/dimethyl-diallylammonium chloride/acrylic acid terpolymer sold under the name MERQUAT 3330DRY POLYMER or MERQUAT 3330PR POLYMER or MERQUAT 3331PR POLYMER or MERQUAT 3940 POLYMER or MERQUAT PLUS 3330 POLYMER OR MERQUAT PLUS 3331 POLYMER by the company Nalco (Lubrizol) (INCI name: Polyquaternium-39); an ampholytic terpolymer consisting of methacrylamidopropyl trimethyl ammonium chloride (MAPTAC), acrylamide and acrylic acid, sold under the name MERQUAT 2003PR POLYMER by the company Nalco (Lubrizol) (INCI name: Polyquaternium-53); Polyquaternium-30, Polyquaternium-35, Polyquaternium-45, Polyquaternium-50, Polyquaternium-54; Polyquaternium-57; Polyquaternium-63; Polyquaternium-74; Polyquaternium-76; Polyquaternium-86; Polyquaternium-87 (polymeric quaternary ammonium salt of vinylpyrrolidone, N-Vinyl Imidazole, and diallyldimethyl ammonium chloride sold under the name LUVIQUAT Sensation by the company BASF); Polyquaternium-89; Polyquaternium-95; Polyquaternium-98, Polyquaternium-104; Polyquaternium-111; Polyquaternium-112, and mixtures thereof.

The compositions of the disclosure preferably contain the cationic agent in an amount of from about 0.05% to about 10% by weight, such as from about 0.1% to about 8% by weight, from about 0.2% to about 7% by weight, from about 0.25% to about 6% by weight, or from about 0.3% to about 5% by weight of active material, based on the total weight of the compositions.

Surfactants

The various compositions described herein may include one or more surfactants, including anionic, non-ionic and/or amphoteric/zwitterionic surfactants. Non-limiting examples of surfactants that may be used are provided below.

Nonionic Surfactants

Examples of nonionic surfactants that may be used are fatty alcohols, alpha-diols and (C1-C24)alkylphenols, these compounds being alkoxylated, polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, polyoxyalkylenated fatty amides, optionally oxyalkylenated alkyl(poly)glucosides, alkylglucoside esters, derivatives of N-alkylglucamine and of N-acylmethylglucamine, aldobionamides, amine oxides and (poly)oxyalkylenated silicones.

Suitable examples are oleth-10, oleth-20, laureth-12, steareth-20, and mixtures thereof.

Other examples of nonionic surfactants that may be used are fatty alcohols such as stearyl alcohol, isostearyl alcohol, cetearyl alcohol, cetyl alcohol, lauryl alcohol, decyl alcohol, and mixtures thereof.

The nonionic surfactants can also be chosen from monooxyalkylenated or polyoxyalkylenated and monoglycerolated or polyglycerolated nonionic surfactants, and alkyl (poly)glucosides. The oxyalkylene units are more particularly oxyethylene or oxypropylene units, or a combination thereof, preferably oxyethylene units.

Useful nonionic surfactants may include: oxyalkylenated (C8-C24)alkylphenols; saturated or unsaturated, linear or branched, oxyalkylenated C8-C40 alcohols; saturated or unsaturated, linear or branched, oxyalkylenated C8-C30 amides; esters of saturated or unsaturated, linear or branched, C8-C30 acids and of polyethylene glycols; saturated or unsaturated, oxyethylenated plant oils; condensates of ethylene oxide and/or of propylene oxide, alone or as mixtures; oxyethylenated and/or oxypropylenated silicones; and alkyl(poly)glucosides.

As examples of monoglycerolated or polyglycerolated nonionic surfactants, monoglycerolated or polyglycerolated C8-C40 alcohols are useable. In particular, the monoglycerolated or polyglycerolated C C8-C40 alcohols correspond to formula (A1) below:

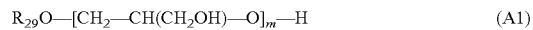

$$R_{29}O-[CH_2-CH(CH_2OH)-O]_m-H \quad (A1)$$

in which formula (A1):

$R_{29}$ represents a linear or branched $C_8$-$C_{40}$ and preferably $C_8$-$C_{30}$ alkyl or alkenyl radical; and m represents a number ranging from 1 to 30, or from 1 to 10.

As examples of compounds of formula (A1), mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A1) may represent a mixture of alcohols in the same way that the value of m represents a statistical value, which means that, in a commercial product, several species of polyglycerolated fatty alcohols may coexist in the form of a mixture.

The alkyl(poly)glycoside nonionic surfactant(s) may be represented by formula (A2) below:

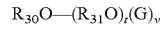

$$R_{30}O-(R_{31}O)_t(G)_v \quad (A2)$$

in which:

R$_{30}$ represents a saturated or unsaturated, linear or branched alkyl group comprising from about 8 to 24 carbon atoms, or an alkylphenyl group in which the linear or branched alkyl group comprises from 8 to 24 carbon atoms;

R$_{31}$ represents an alkylene group containing from about 2 to 4 carbon atoms, G represents a saccharide unit comprising from 5 to 6 carbon atoms, t denotes a value ranging from 0 to 10, or from 0 to 4, and v denotes a value ranging from 1 to 15.

In some cases, the alkyl(poly)glycoside nonionic surfactant(s) correspond to formula (IX) in which:

R$_{30}$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and R$_{31}$ and v are as defined previously.

The degree of polymerization of the alkyl(poly)glucoside nonionic surfactant(s), as represented, for example, by the index v in formula (IX), ranges on average from 1 to 15, or from 1 to 4. This degree of polymerization more particularly ranges from 1 to 2 and better still from 1.1 to 1.5, on average.

The glycoside bonds between the saccharide units are of 1.6 or 1.4 type and preferably of 1.4 type.

Examples of compounds of formula (A2) that may especially be mentioned are decyl glucoside, coco-glucoside, lauryl glucoside, such as the products sold by the company Cognis under the names PLANTAREN (600 CS/U, 1200 and 2000) or PLANTACARE (818, 1200 and 2000). Use may also be made of the products sold by the company SEPPIC under the names TRITON CG 110 (or ORAMIX CG 110) and Triton CG 312 (or ORAMIX NS 10), the products sold by the company BASF under the name LUTENSOL GD 70 or the products sold by the company Chem Y under the name AG10 LK. Use may also be made, for example, of the 1,4-(C8-C16)alkylpolyglucoside as an aqueous solution at 53% by weight relative to the total weight of the solution, sold by Cognis under the reference PLANTACARE 818 UP.

Amphoteric or Zwitterionic Surfactants

The amphoteric or zwitterionic surfactant that may be used in compositions according to the disclosure may be derivatives of aliphatic secondary or tertiary amines, optionally quaternized, in which derivatives the aliphatic group is a linear or branched chain comprising from 8 to 22 carbon atoms, the amine derivatives containing at least one anionic group, such as a carboxylate, sulfonate, sulfate, phosphate or phosphonate group. Mention may be made in particular of (C8-C20)alkylbetaines such as cocoylbetaine, sulfobetaines, (C8-C20)alkylamido(C2-C8)alkylbetaines such as cocoylamidopropylbetaine or (C8-C20)alkylamido(C6-C8)-alkylsulfobetaines, and mixtures thereof.

Among the derivatives of aliphatic secondary or tertiary amines, optionally quaternized, that may be used, as defined above, mention may also be made of the compounds of respective structures (I), (II) and (IIa) below:

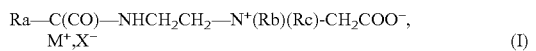

$$Ra—C(CO)—NHCH_2CH_2—N^+(Rb)(Rc)\text{-}CH_2COO^-,\ M^+, X^- \quad (I)$$

in which formula (I):

Ra represents a C10-C30 alkyl or alkenyl group derived from an acid Ra—COOH preferably present in hydrolysed coconut oil, or a heptyl, nonyl or undecyl group;

R$^b$ represents a beta-hydroxyethyl group; and

Rc represents a carboxymethyl group;

M+ represents a cationic counterion derived from an alkali metal or alkaline-earth metal, such as sodium, an ammonium ion or an ion derived from an organic amine; and X– represents an organic or mineral anionic counterion, such as that chosen from halides, acetates, phosphates, nitrates, (C1-C4)alkyl sulfates, (C1-C4)alkyl- or (C1-C4) alkylarylsulfonates, in particular methyl sulfate and ethyl sulfate; or alternatively M+ and X– are absent;

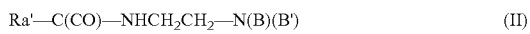

$$Ra'—C(CO)—NHCH_2CH_2—N(B)(B') \quad (II)$$

in which formula (II):

B represents the group —CH2-CH2-O—X';

B' represents the group —(CH2)zY', with z=1 or 2;

X' represents the group —CH2-COOH, CH2-COOZ', —CH2CH2-COOH or —CH2CH2-COOZ', or a hydrogen atom;

Y' represents the group —COOH, —COOZ', CH2CH(OH)SO3H or the group —CH2CH(OH)SO3Z';

Z' represents a cationic counterion derived from an alkali metal or alkaline-earth metal, such as sodium, an ammonium ion or an ion derived from an organic amine;

Ra' represents a C10-C30 alkyl or alkenyl group of an acid Ra'—COOH, which may be coconut oil or in hydrolysed linseed oil, or an alkyl group, especially a C17 group and its iso form, or an unsaturated C17 group.

The compounds of this type are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylam phodi propionate, disodium capryloamphodipropionate, lauroamphodipropionic acid and cocoamphodipropionic acid.

By way of example, mention may be made of the cocoamphodiacetate sold by the company Rhodia under the trade name Miranol C2M Concentrate and the cocoamphodipropionate sold by the company Evonik Goldschmidt under the trade name Rewoteric AM KSF 40.

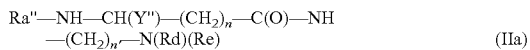

$$Ra''—NH—CH(Y'')—(CH_2)_n—C(O)—NH\\—(CH_2)_{n'}—N(Rd)(Re) \quad (IIa)$$

in which formula (IIa):

Y'' represents the group —COOH, —COOZ'', —CH2CH(OH)SO3H or the group —CH2CH(OH)SO3Z'';

Rd and Re, independently of each other, represent a C1-C4 alkyl or hydroxyalkyl radical;

Z'' represents a cationic counterion derived from an alkali metal or alkaline-earth metal, such as sodium, an ammonium ion or an ion derived from an organic amine;

Ra'' represents a C10-C30 alkyl or alkenyl group of an acid Ra''—COOH;

n and n' denote, independently of each other, an integer ranging from 1 to 3; and mixtures of these compounds.

Among the compounds of formula (IIa), mention may be made of the compound classified in the CTFA dictionary under the name sodium diethylaminopropyl cocoaspartamide and sold by the company Chimex under the name Chimexane HB. In some instances, the amphoteric or zwitterionic surfactant(s) are chosen from cocoylbetaine, cocoylamidopropylbetaine and sodium cocoylamidoethyl-N-hydroxyethylaminopropionate.

Anionic Surfactants

The term "anionic surfactant" means a surfactant comprising, as ionic or ionizable groups, only anionic groups. These anionic groups are chosen preferably from the groups CO2H, CO2-, SO3H, SO3-, OSO3H, OSO3-O2PO2H, O2PO2H and O2PO22-.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acyl isethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of C6-C24 alkyl monoesters of polyglycoside-polycarboxylic acids may be chosen from C6-C24 alkyl polyglycoside-citrates, C6-C24 alkyl polyglycoside-tartrates and C6-C24 alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of (C6-C24)alkyl sulfates, (C6-C24) alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferably, the anionic surfactant(s) are chosen from (C10-C20)alkyl ether sulfates, and in particular sodium lauryl ether sulfate containing 2.2 mol of ethylene oxide.

The compositions of the disclosure preferably contain the cationic agent in an amount of from about 0.05% to about 20% by weight, such as from about 0.1% to about 15% by weight, from about 0.2% to about 12% by weight, from about 0.25% to about 10% by weight, or from about 0.3% to about 8% by weight of active material, based on the total weight of the compositions.

Silicones

The compositions of the present disclosure may further comprise one or more silicone compounds. The one or more silicone compounds may be chosen from amino silicones and non-amino silicones (no amino groups) such as dimethicone, and mixtures thereof.

In an embodiment, the one or more silicone compounds of the present disclosure is an amino silicone.

The term "amino silicone" is intended to mean any silicone comprising at least one primary, secondary or tertiary amine or a quaternary ammonium group (i.e., a quaternized group).

As amino silicone that may be used in the scope of the instant disclosure, the following can be cited:

a) polysiloxanes corresponding to formula (A):

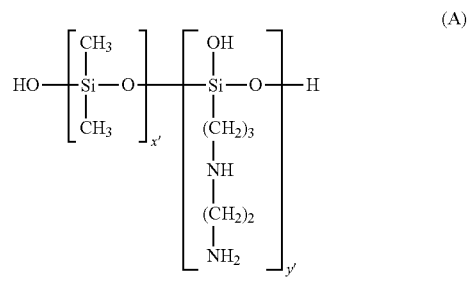

in which x' and y' are integers such that the weight-average molecular weight (Mw) is comprised between about 5000 and 500 000;

b) amino silicones corresponding to formula (B):

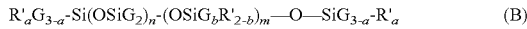

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —$C_qH_{2q}L$ in which q is a number ranging from 2 to 8 and L is an optionally quaternized amino group chosen from the following groups:

—NR"-Q-N(R")$_2$
—N(R")$_2$
—N+(R")$_3$A-
—N+H(R")$_2$A-
—N+H$_2$(R") A-
—N(R")-Q-N+R"H$_2$A-
—NR"-Q-N+(R")$_2$HA-
—NR"-Q-N+(R")$_3$A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

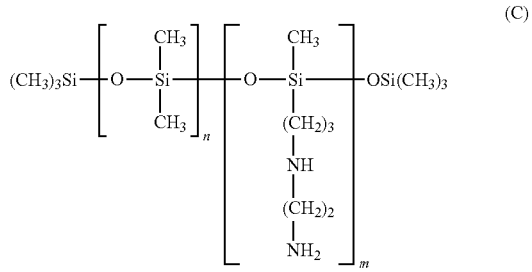

in which n and m have the meanings given above, in formula B.

Another group of amino silicones corresponding to this definition is represented by silicones having the following formulae (D) or (E):

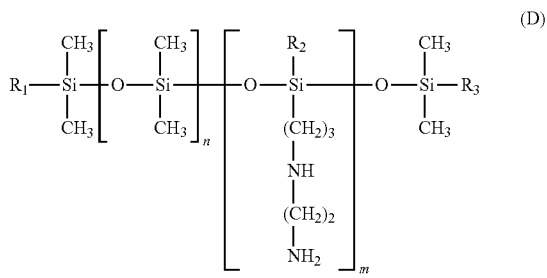

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

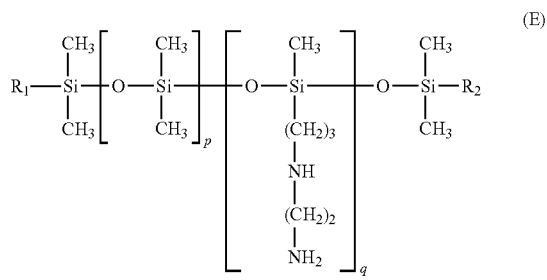

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300e.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometers. Preferably, in particular as amino silicones having formula (E), microemulsions are used whose average particle size ranges from 5 nm to 60 nanometers (limits included) and more preferably from 10 nm to 50 nanometers (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

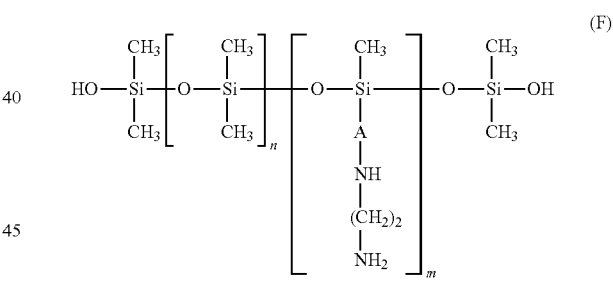

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

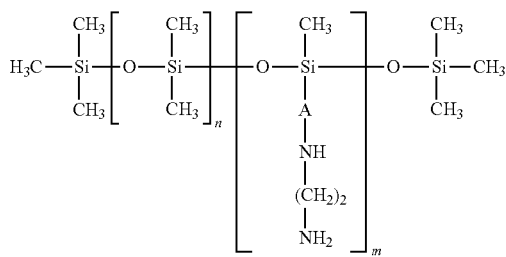

(G)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

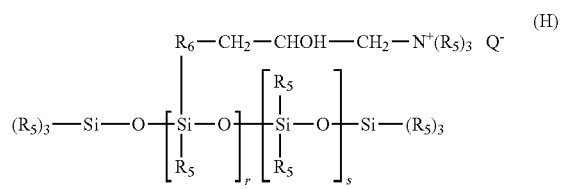

(H)

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in U.S. Pat. No. 4,185,087.

d) quaternary ammonium silicones having formula (I):

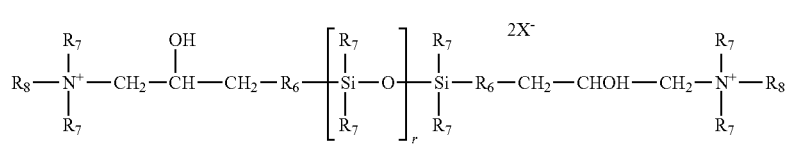

(I)

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

X- is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

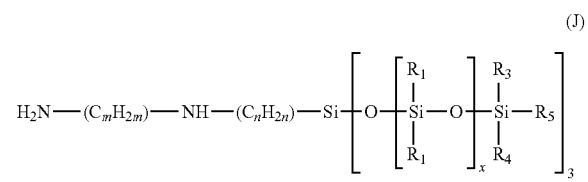

(J)

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

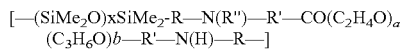

or alternatively

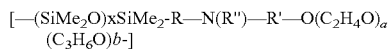

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

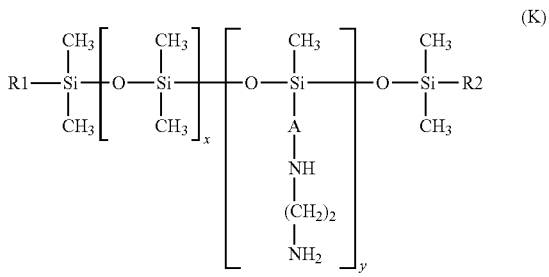

in which:

x and y are numbers ranging from 1 to 5000; preferably, x ranges from 10 to 2000 and especially from 100 to 1000; preferably, y ranges from 1 to 100;

$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;

A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$ and —$CH_2CH(CH_3)CH_2$—.

Preferably, R1 and R2, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, R1 and R2, which may be identical or different, are chosen from hexadecyl (cetyl) and octadecyl (stearyl) radicals.

Preferentially, the silicone is of formula (K) with:

x ranging from 10 to 2000 and especially from 100 to 1000;

y ranging from 1 to 100;

A comprising 3 to 6 carbon atoms and especially 4 carbon atoms; preferably, A is branched; and more particularly A is chosen from the following divalent radicals: $CH_2CH_2CH_2$ and —$CH_2CH(CH_3)CH_2$—; and $R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

h) silicone compounds with at least one quaternary ammonium group.

Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Most preferred are quaternium 80, silicone quaternium-16, silicone quaternium-18, silicone quaternium-15, and mixtures thereof.

The silicone compounds with at least one quaternary ammonium group can also include those compounds of formula (B) when L in formula (B) is a quaternized amino group as described.

In an embodiment, the one or more silicone compounds of the present disclosure is a non amino silicone compound such as a dimethicone compound.

In an embodiment, the one or more silicone compounds of the present disclosure is an amino silicone compound such as amodimethicone.

The silicone compound of the present disclosure may be provided or may be commercially available in emulsion form that further comprises surfactants chosen from nonionic surfactants, cationic surfactants, and mixtures thereof. In certain embodiments, the emulsion in which the silicone compound is contained is a microemulsion.

The silicone compound(s) may be present in the composition according to the invention in an amount of about 0.05% to about 5% by weight, such as from about 0.1% to about 4% by weight, from about 0.15% to about 3% by weight, from about 0.2% to about 3% by weight, or from about 0.3% to about 2.5%, by weight of the active material, based on the total weight of the composition, including all ranges and subranges therebetween.

In some embodiments, the silicone compound(s) may be introduced into the compositions of the invention in the form of an emulsion material in an amount of about 0.05% to about 8% by weight, such as from about 0.1% to about 7% by weight, from about 0.15% to about 6% by weight, from about 0.2% to about 5% by weight, or from about 0.3% to about 4%, by weight of the active material, based on the total weight of the compositions, including all ranges and subranges therebetween.

In various embodiments, the total amount of silicone compound(s) is about 0.01%, 0.025%, 0.04%, 0.05%, 0.075%, 0.1%, 0.15%, 0.2%, 0.25%, 0.3%, 0.325%, 0.35%, 0.4%, 0.44%, 0.45%, 0.5%, 0.55%, 0.6%, 0.64%, 0.65%, 0.7%, 0.75%, 0.774%, 0.8%, 0.85%, 0.88%, 0.9%, 0.95%, 1%, 1.25%, 1.5%, 1.75%, 2%, 2.25% 2.5%, 2.75%, 3%, 3.25% 3.5%, 3.75%, or 4% by weight of the active material or the emulsion material, based on the total weight of the composition.

Conditioning Agents

The compositions may contain one or more conditioning agents such as esters, oils, emollients, and mixtures thereof.

Forms

The compositions described herein may be in any suitable physical form. Suitable forms include, but are not limited to, low to moderate viscosity liquids, creams, lotions, milks, mousses, sprays, gels, and the like. Suitable excipients, such as those listed above, are included or excluded from the hair coloring formulation depending on the form of use of the formulation (e.g., spray, cream, gel, etc.).

i. Creams

The compositions disclosed herein for coloring hair may be in the form of a cream. The cream can be prepared as emulsions, for example, oil in water or water in oil or water in oil in water emulsions and will generally contain one or more of emulsifying agents, nonionic surfactants, anionic surfactants, cationic agents, conditioning agents, fatty alcohols, oils, and mixtures thereof.

ii. Gels

The compositions disclosed herein for coloring hair may be in the form of a gel. The gels will typically contain a cosmetically acceptable carrier such as water and will generally contain one or more of gelling agents, structuring agents, rheology or viscosity modifying agents, and mixtures thereof.

iii. Spray

The compositions described herein for coloring hair may be in the form of a spray. The spray typically includes the coloring composition in a cosmetically acceptable carrier. In some embodiments, the carrier is water or a water and alcohol mixture. The spray formulation optionally includes an emollient, thickener, hair conditioning agent, polymer, and/or surfactant. The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair color formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

Kits and Methods

Other aspects of the invention pertain to kits comprising various combinations of the pre-color treatment, coloring and developer compositions described herein. For example, the developer may be present in a separate container from the coloring composition. The coloring composition may, in some embodiments, be ready for mixing with the developer. In such embodiments, the developer and hair coloring composition are combined just prior to use.

In other embodiments, each of the above-described components (pre-color treatment composition comprising the metal salts and antioxidants, coloring composition, and developer) are packaged in separate containers.

In an embodiment, the one or more divalent metal salts of an inorganic acid, the one or more monovalent or divalent metal salts of an organic acid, the one or more antioxidants, and the hair coloring composition containing one or more colorants chosen from oxidative dye precursors, direct dyes, pigments, and mixtures thereof, are packaged in separate containers.

In an embodiment, the one or more divalent metal salts of an inorganic acid and the one or more monovalent or divalent metal salts of an organic acid are packaged together in one container and the one or more antioxidants are packaged in another container.

In yet another embodiment, each of the one or more divalent metal salts of an inorganic acid, the one or more monovalent or divalent metal salts of an organic acid, and the one or more antioxidants are provided as separate compositions and packaged in different containers.

The pre-color treatment composition or each of the metal salt components (metal salts of an inorganic acid and monovalent or divalent metal salts of an organic acid), and the antioxidant or in various combinations thereof, can be in liquid form (for example, aqueous form in water or emulsion/lotion form or serum) or in powder form).

In an embodiment, the pre-color treatment composition is in powder form.

Another aspect of the invention pertains to methods of using the pre-color treatment compositions. The methods comprise applying the pre-color treatment compositions or metal salt and antioxidant components in a sequential manner described herein to human hair in any order. The pre-color treatment composition or components may be left on the hair for a period of time for up to two hours, such as from about 30 seconds to about 90 minutes, from about 30 seconds to about 60 minutes, from about 30 seconds to about 45 minutes, from about 1 minute to about 30 minutes, or from about 5 minutes to about 20 minutes. In further embodiments, the dye composition may be left on the hair for a period up to about 30 minutes, such as, for example, from about 1 to about 30 minutes, about 1 to about 10 minutes, or about 1 to about 5 minutes, or about 10 seconds to about 1 minute.

The methods of the present disclosure also involve dyeing the hair after treating the hair with the pre-color treatment composition of the present disclosure with the dye compositions resulting from the combination of the coloring composition and oxidizing composition (developer). The methods comprise applying the dye compositions described herein to human hair after treating the hair with the pre-color treatment composition. The dye composition may be left on the hair for a period of time sufficient to achieve the desired alteration in hair tone. For example, the dye composition may be left on the hair for up to one hour, such as from about 3 minutes to about 45 minutes, from about 5 minutes to about 30 minutes, or from about 10 minutes to about 20 minutes. In further embodiments, the dye composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the dye composition on the hair in order to achieve the desired alteration in hair tone. By way of non-limiting example, various embodiments according to the disclosure may provide for an increase of 1 to 4 in the tone height of the hair.

In an embodiment, the hair treated with the pre-color treatment composition of the present disclosure is not rinsed or washed with water or a shampooed/washed before dyeing the hair.

In an embodiment, the hair treated with the pre-color treatment composition of the present disclosure is rinsed or washed with water or shampooed/washed before dyeing the hair.

In some embodiments, the dye composition may, optionally, be shampooed and/or rinsed off the hair.

In preferred embodiments, the dye composition is shampooed and/or rinsed off the hair.

Implementation of the present disclosure is provided by way of the following examples. The examples serve to illustrate the technology without being limiting in nature.

EXAMPLES

General Procedures

Regular bleached hair swatches (from International Hair Importers, IHIP) were treated and evaluated as set forth below.

General Coloration Process: The hair swatches were colored/dyed with a dye mixture formed from combining a coloring composition and a developer composition for a period of time to give a desired color to the hair. The coloring composition (typically, in the form of a cream or an emulsion cream) contained oxidative dyes and the developer contained an oxidizing agent (hydrogen peroxide). The developer composition can employ different amounts of the oxidizing agent depending on the desired lift or lightening of the color on the hair. For example, a 20 volume developer means that it contains 6 wt. % of an oxidizing agent; a 10 volume developer means that it contains 3 wt. % of an oxidizing agent; a 3 volume developer means that it contains 0.9 wt. % of an oxidizing agent.

The weight ratio of the coloring composition to the developer in the present disclosure can range from about 1:4 to about 5:0.2, or from about 1:3 to about 4.8:0.2, or from about 1:2 to about 4.8:0.2, or from about 1.5:2 to about 4.8:0.2, or from about 1.5:2.25 to about 4.8:0.2, or from about 1:2 to about 2:1, or from about 1:1 to about 4.8:0.2, including ranges and sub-ranges therebetween.

In various embodiments, the weight ratio of the coloring composition to the developer in the present disclosure is at about 2:3, or about 3:3, or about 1:2, or about 2:2, or about 1:1, or about 1.5:2, or about 1.5:2.25, or about 1:1.5, or about 1.5:1.5 (or 1), or about 1.5:2.5, or about 4:1, or about 3:0.5, or about 4.8:0.2, including ranges and sub-ranges therebetween.

Example 1 Color Protection

Assessing the efficacy of a pre-color treatment containing Zinc Gluconate, Calcium Chloride, and Ascorbic Acid for hair color protection or durability of color against shampooing.

Pre-Color Treatment:

TABLE 1

Salt composition

| Ingredient INCI US NAME | Wt. % |
|---|---|
| CALCIUM CHLORIDE | 5 |
| PHENOXYETHANOL | 0.9 |
| HYDROXYPROPYL GUAR | 0.6 |
| ZINC GLUCONATE | 5 |
| AMODIMETHICONE | 2.57 |
| ETHYLHEXYLGLYCERIN | 0.1 |
| WATER | 85.33 |
| HYDROXYETHYLCELLULOSE | 0.5 |

TABLE 2

Antioxidant composition

| Ingredient INCI US NAME | Wt. % |
|---|---|
| ASCORBIC ACID | 100 |

The salt composition in Table 1 above was combined with ascorbic acid from Table 2, in a 5:1 ratio in order to form the pre-color treatment (salt-antioxidant composition). The hair swatches were then treated with the pre-color treatment after which they were allowed to stand at room temperature for 20 minutes.

Color Treatment:

The treated hair swatches and untreated hair swatches (control) were colored using a hair coloring product (1 g color cream/2.25 g developer of 20 vol peroxide developer (hydrogen peroxide)/1 g hair) for a period of time (30 minutes) to give the hair a desired color (intense auburn) after which the hair was rinsed and dried to remove excess dye.

Hair Shampooing:

The colored/treated and untreated hair swatches were washed with an anionic shampoo (containing 12 wt. % sodium laureth sulfate, pH=5.5) 5 times. The hair swatches were rinsed with water and blown dry. This was repeated 3 times for a total of 15 times (15 shampoos).

Color Assessment:

For determining the degree of change in the color of hair (e.g. degree of lightening of the color or color deposit), measurements of L*, a*, and b* values of the hair swatches were obtained before and after 10 shampoos. The L*a*b* colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively. The higher the L*, the lighter the color of the hair; the higher the a*, the more the hue shifts to red (i.e., the hair is redder); and the lower the b*, the more the chroma value shifts to blue. Delta-E (LE or dE) which is calculated from the L*, a*, and b* values represents the overall color change on the swatches (from control or baseline).

TABLE 3

Results

| Treatment | Zinc Gluconate Wt. % | Calcium Chloride Wt. % | Ascorbic Acid Wt. % | dE @ 15x Shampoo |
|---|---|---|---|---|
| Standard | — | — | — | 7.06 |
| Pre-color treatment with salts (Control) | 5 wt % | 5 wt % | | 8.18 |
| Pre-color treatment with antioxidant (Control) | | | 20 Wt % | 6.76 |
| Pre-color treatment (Invention) | 5 wt % | 5 wt % | 20 wt % | 6.17 |

As shown by the data in the table above, hair treated with the solution containing zinc gluconate+calcium chloride+ascorbic acid as a pre-color treatment surprisingly and unexpectedly retained its color more than the hair treated with the standard and each control (zinc gluconate+calcium chloride and ascorbic acid alone) after 15 shampoos. The control treatment with the salts resulted in the greatest color change or color loss as compared to the other treatments. On the hand, while the control treatment with ascorbic acid alone resulted in less color change or color loss as compared to the control treatment with salts, the color change or color loss was still greater than the color change with the pre-color treatment containing zinc gluconate+calcium chloride+ascorbic acid.

The results above show that unexpectedly, it was found that the inventive pre-color treatment composition protected the color of the colored hair from fading as evident from the lower ΔE values as compared to the values measured from Swatches treated with the standard and control pre-color treatments. The lower ΔE indicates a lower change between the initial color and the color after 15 shampoo cycles (less color loss).

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about," if desired to impart the meaning above, or recited without the term in order to have their ordinary meaning, regardless of whether the term "about" is specifically set forth (or is absent) in conjunction with any particular value in the specification.

When referring to "compositions described herein," all types of compositions are intended unless specifically described otherwise.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for artificially coloring hair and inhibiting the coloring from fading, the method comprising:
   (a) treating hair with a pre-color treatment composition comprising:
      at least 0.5 wt. % of one or more divalent metal salts of an inorganic acid;
      at least 0.5 wt. % of one or more monovalent or divalent metal salts of an organic acid; and
      at least 0.5 wt. % of one or more antioxidants;
      all weights being based on the total weight of the pre-color treatment composition; and
   (b) treating the hair with a hair coloring composition comprising one or more colorants chosen from oxidative dye precursors, direct dyes, pigments, and mixtures thereof.

2. The method of claim 1, wherein the one or more divalent metal salts of an inorganic acid are chosen from metal halides, metal hydroxides, metal sulfates, metal oxides, and mixtures thereof.

3. The method of claim 1, wherein the one or more divalent metal salts of an inorganic acid are chosen from salts of calcium, zinc, iron, nickel, copper, silver, magnesium, strontium, barium, manganese, cobalt, and mixtures thereof.

4. The method of claim 1, wherein the one or more divalent metal salts of an organic acid are chosen from salts of calcium, zinc, iron, nickel, copper, silver, magnesium, strontium, barium, manganese, cobalt, and mixtures thereof and wherein the one or more monovalent metal salts of an organic acid are chosen from salts of lithium, sodium, potassium, copper, silver, and mixtures thereof.

5. The method of claim 1, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

6. The method of claim 1, wherein the one or more divalent metal salts of an inorganic acid includes a calcium salt.

7. The method of claim 6, wherein the calcium salt is calcium chloride.

8. The method of claim 1, wherein the organic acid of the one or more monovalent or divalent metal salts of an organic acid is chosen from C1 to C9 monocarboxylic or di-carboxylic acids, polycarboxylic acids, hydroxy-carboxylic acids, and fatty acids having at least 10 carbon atoms, or compounds with heterocyclic groups containing one or more carboxyl groups.

9. The method of claim 1, wherein the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

10. The method of claim 1, wherein the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

11. The method of claim 1, wherein the one or more antioxidants are chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof.

12. The method of claim 1, wherein the one or more divalent metal salts of an inorganic acid is chosen from calcium chloride; the one or more divalent metal salts of an organic acid is chosen from zinc gluconate; and the one or more organic acids is chosen from ascorbic acid.

13. The method of claim 1, wherein the pre-color treatment composition comprises from about 0.5 wt. % to about 50 wt. % of one or more divalent metal salts of an inorganic acid, based on the total weight of the pre-color treatment composition; from about 0.5 wt. % to about 50 wt. % of one or more monovalent or divalent metal salts of an organic acid, based on the total weight of the pre-color treatment composition; and from about 0.5 wt. % to about 50 wt. % of one or more antioxidants, based on the total weight of the pre-color treatment composition.

14. The method of claim 1, wherein the weight ratio of the one or more divalent metal salts of an inorganic acid to the one or more monovalent or divalent metal salts of an organic acid is from about 10:1 to about 1:10.

15. The method of claim 1, wherein the weight ratio of the one or more divalent metal salts of an inorganic acid to the one or more monovalent or divalent metal salts of an organic acid is from about 1.55 to about 1.

16. The method of claim 1, wherein the weight ratio of the total amount of the one or more divalent metal salts of an inorganic acid and the one or more monovalent or divalent metal salts of an organic acid to the amount of the one or more antioxidants is from about 1:15 to about 1:2.

17. The method of claim 1, wherein the hair coloring composition further comprises one or more oxidizing agents or is capable of being mixed with an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

18. The method of claim 1, further comprising forming the pre-color treatment composition by combining a first composition containing the one or more divalent metal salts of an inorganic acid and the one or more monovalent or divalent metal salts of an organic acid with a second composition containing the one or more antioxidants within 2 hours before artificially coloring hair.

19. The method of claim 18, wherein the first composition and/or the second composition is in powder form.

20. The method of claim 1, wherein the pre-color treatment composition further comprises one or more of a thickening agent, a cationic agent, a surfactant, a silicone, and a cosmetically acceptable solvent.

21. The method of claim 1, wherein the pre-color treatment composition is allowed to remain on the hair for at least 30 seconds before treating the hair with the hair coloring composition.

22. The method of claim 1, wherein the pre-color treatment composition is allowed to remain on the hair for about 1 minute to about 1 hour at a temperature of about 20° C. to about 45° C. before treating the hair with the hair coloring composition.

23. A multi-compartment kit for altering the color of hair, the kit comprising:
  (i) a pre-color treatment component comprising one or more divalent metal salts of an inorganic acid; one or more monovalent or divalent metal salts of an organic acid; and one or more antioxidants;
  (ii) a hair coloring composition comprising one or more colorants chosen from oxidative dye precursors, direct dyes, pigments, and mixtures thereof; and
  (iii) an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

24. The kit of claim 23, wherein the pre-color treatment component comprises a first composition containing the one or more divalent metal salts of an inorganic acid and the one or more monovalent or divalent metal salts of an organic acid; and a second composition containing the one or more antioxidants.

25. The kit of claim 23, wherein the one or more divalent metal salts of an inorganic acid are present in an amount of at least 0.5 wt. %, based on the total weight of the pre-color treatment component, and are chosen from metal halides, metal hydroxides, metal sulfates, metal oxides, and mixtures thereof; and wherein the divalent metal is calcium, zinc, iron, nickel, copper, silver, magnesium, strontium, barium, manganese, or cobalt;
  the one or more monovalent or divalent metal salts of an organic acid are present in an amount of at least 0.5 wt.

%, based on the total weight of the pre-color treatment component, and are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof; wherein the monovalent metal is lithium, sodium, potassium, copper, or silver; and wherein the divalent metal is calcium, zinc, iron, nickel, copper, silver, magnesium, strontium, barium, manganese, or cobalt; and the one or more antioxidants are present in an amount of at least 0.5 wt. %, based on the total weight of the pre-color treatment component and are chosen from ascorbic acid, sodium sulfite, sodium metabisulfite, sodium hydrosulfite, tocopherols, alpha-tocopherol, tocopheryl acetate, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, and mixtures thereof.

26. The kit of claim 23, wherein the pre-color treatment composition further comprises one or more of a thickening agent, a cationic agent, a surfactant, a silicone, and a cosmetically acceptable solvent.

27. A pre-color treatment composition comprising:
about 0.5 wt. % to about 20 wt. % of one or more divalent metal salts of an inorganic acid chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; and about 0.5 wt. % to about 20 wt. % of one or more monovalent or divalent metal salts of an organic acid chosen from zinc lactate, zinc gluconate, zinc phenolsulfonate, zinc salicylate, zinc pyrrolidone carboxylic acid (Zinc PCA), zinc citrate, zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof; and about 0.5 wt. % to about 30 wt. % of one or more antioxidants are chosen from ascorbic acid and its derivatives, sodium sulfite, sodium metabisulfite, sodium hydrosulfite, tocopherols, alpha-tocopherol, tocopheryl acetate, EDTA, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, Butylated hydroxytoluene (BHT), Butylated hydroxyanisole (BHA), N,N'-bis(3,4,5-trimethoxybenzyl)ethylenediamine and its salts, and mixtures thereof;

all weights being based on the total weight of the composition.

28. The pre-color treatment composition of claim 27, comprising a first composition containing the one or more divalent metal salts of an inorganic acid and the one or more monovalent or divalent metal salts of an organic acid; and a second composition containing the one or more antioxidants; wherein the first and the second compositions are combined within 2 hours before artificially coloring hair.

29. The pre-color treatment composition of claim 27, further comprising one or more of a thickening agent, a cationic agent, a surfactant, a silicone, and a cosmetically acceptable solvent.

30. The pre-color treatment composition of claim 27, wherein the weight ratio of the one or more divalent metal salts of an inorganic acid to the one or more monovalent or divalent metal salts of an organic acid is from about 10:1 to about 1:10.

* * * * *